United States Patent [19]

Lee et al.

[11] Patent Number: 5,516,952
[45] Date of Patent: *May 14, 1996

[54] OXIDATIVE DECOUPLING OF SCRAP RUBBER

[75] Inventors: Sunggyu Lee, Akron; Fouad O. Azzam, Canton; Brian S. Kocher, Akron, all of Ohio

[73] Assignee: The University of Akron, Akron, Ohio

[*] Notice: The term of this patent shall not extend beyond the expiration date of Pat. No. 5,386,055.

[21] Appl. No.: 354,526

[22] Filed: Dec. 13, 1994

Related U.S. Application Data

[63] Continuation-in-part of Ser. No. 105,881, Aug. 11, 1993, abandoned.

[51] Int. Cl.$^6$ .................................................. C07C 1/00
[52] U.S. Cl. ........................................... 585/241; 585/832
[58] Field of Search ............................... 585/241, 832

[56] References Cited

U.S. PATENT DOCUMENTS

| | | |
|---|---|---|
| T965,002 | 12/1977 | Crane et al. . |
| 4,031,192 | 6/1977 | Hälfeli . |
| 4,179,263 | 12/1979 | June et al. . |
| 4,338,199 | 7/1982 | Modell . |
| 4,533,463 | 8/1985 | Yan et al. . |
| 4,543,190 | 9/1985 | Modell . |
| 4,657,681 | 4/1987 | Hughes et al. . |
| 4,898,107 | 2/1990 | Dickinson . |
| 5,087,436 | 2/1992 | Roy . |
| 5,106,513 | 4/1992 | Hong . |
| 5,136,111 | 8/1992 | Chum et al. . |
| 5,216,149 | 6/1993 | Evans et al. . |
| 5,280,701 | 1/1994 | Tolman . |
| 5,386,055 | 1/1995 | Lee et al. ................... 562/512.2 |

OTHER PUBLICATIONS

An article entitled "Catalytic Selective Oxidation (ACS Symposium Series 523)", dated Aug. 23–28, 1992, Oyama and Hightower.

*Primary Examiner*—Asok Pal
*Assistant Examiner*—Bekir L. Yildirim
*Attorney, Agent, or Firm*—Renner, Kenner, Greive, Bobak, Taylor & Weber

[57] ABSTRACT

A process for breaking down rubber polymer materials by selective oxidative decoupling of carbon-carbon, carbon-sulfur and sulfur-sulfur bonds at supercritical or near supercritical conditions for water and wherein supercritical water or water near supercritical conditions is used as a solvent and reforming agent, is used to produce relatively high yields of lower molecular weight hydrocarbons and oxygenated hydrocarbons which are suitable for use as a fuel or which can be separated or further refined to produce various commodity chemicals, specialty chemicals or both. The invention provides an environmentally friendly process for recycling rubber waste materials such as waste tires to generate valuable fuels or chemical feedstocks in a closed oxidation process which is free of hazardous stack emissions. The rubber polymer materials which can be recycled in accordance with the process can include typical amounts of conventional compounding ingredients and other impurities without significantly affecting the overall conversion.

14 Claims, 3 Drawing Sheets

OXIDATIVE DECOUPLING OF SCRAP RUBBER

CROSS REFERENCE

This application is a Continuation-In-Part application of U.S. Ser. No. 08/105,881, filed Aug. 11, 1993, now abandoned.

FIELD OF THE INVENTION

The invention relates generally to a method for recovering commercially valuable products from scrap rubber, and more particularly to a selective oxidative decoupling process for converting polymeric elastomers into lower molecular weight compounds which can be used as chemical feedstocks, such as for repolymerization into pure or virgin rubber polymer, or which can be used as a fuel.

BACKGROUND

Conventional methods of recycling waste rubber from tires generally involve size reduction and mechanical removal of the steel belts, followed by defibering with chemicals such as zinc or calcium chlorides, and exposure to high temperature for prolonged periods of time to achieve some carbon-carbon bond cleavage to form three-dimensional, crosslinked rubber fragments which can be recompounded to form lower-grade products such as automobile floor mats. Reclaimed rubber fragments can also be used in relatively small amounts to form products such as semi-pneumatic tires and inner tubes. It is also known to use conventional reclaimed rubber as an additive to asphalt to inhibit flow at elevated temperatures while also improving low-temperature flexibility. However, the relatively meager demand for reclaimed rubber from scrap tires for use in asphalt, floor mats and other low-grade products is overwhelmingly outweighed by the ever burgeoning accumulation of scrap tires at landfill and other waste gathering sites.

Accumulation of scrap tires represents a major environmental problem by presenting a serious risk of potential environmental damage by ignition thereof, for example by lightening or by vandals. Another disadvantage is that tires do not decompose under conditions encountered at waste gathering sites and, therefore, represent an ever increasing volume of material occupying dwindling amounts of available space for waste disposal. At the same time, scrap tires and other scrap rubber can represent a significant source of energy and valuable chemical feedstocks.

Ground rubber materials have been used directly as a fuel and/or in combination with other fuels. However, the direct combustion of waste rubber is generally unacceptable due primarily to the difficulty of obtaining complete combustion. In particular, the amount of mechanical energy needed to achieve a sufficient particle size reduction to effect complete combustion of the rubber would make it uneconomical and impractical to use waste rubber as a fuel. As a result, the use of waste rubber as a fuel has generally resulted in incomplete combustion, undesirable stack emissions, fouling of the combustion apparatus, and high amounts of residue and ash.

U.S. Pat No. 4,740,270 to Roy discloses a method for the treatment of used tires by vacuum pyrolysis to produce liquid and gaseous hydrocarbons and a solid carbonaceous material. The pyrolysis is carried out at a temperature of about 350° to about 415° C. and under a subatmospheric pressure of less than about 35 mm Hg to produce a pyrolytic oil typically containing about 60 weight percent hydrocarbon oils, about 38 weight-percent solid carbonaceous material, and about 2 weight percent gaseous hydrocarbons. The pyrolytic oil is reported to have a heating value of about 10,200 kcal per kg. The process has the disadvantage that only about 60 percent of the rubber waste is converted to a liquid fuel.

SUMMARY OF THE INVENTION

In accordance with the process of the invention, it has been discovered that various natural and synthetic, vulcanized and non-vulcanized rubbers can be oxidatively decoupled by selective partial oxidation in a super-critical water mixture or in a water mixture near super-critical conditions. Specifically, it has been found that various rubber polymers can be oxidatively devulcanized and broken down into smaller components by carbon-carbon, carbon-sulfur and sulfur-sulfur bond scission to produce high yields of lower alkanes, alkenes, dienes, aromatics, alcohols, carboxylic acids, aldehydes, ketones and other lower molecular weight hydrocarbons and oxygenated hydrocarbons. Various rubber compositions can be oxidatively decoupled using the process of the invention to produce commercially useful products such as, for example, combustible liquid fuels and chemical feedstocks.

Oxidative decoupling in accordance with the process of the invention is achieved by forming a homogeneous or pseudohomogeneous mixture of a suitable rubber polymer, including both addition and condensation type rubber polymers, water at supercritical conditions, and an amount of an oxidant which is effective to cause selective oxidative decoupling of the rubber polymer. The super-critical water is used as both a solvent and reforming agent for the rubber polymer. At supercritical water conditions, oxygen and nitrogen are completely miscible with water in all proportions creating a single fluid phase in contact with the rubber polymer. The rubber polymer is preferably comminuted to form small particles which are dispersed in the supercritical fluid. The rubber polymer swells and dissolves or at least becomes intimately dispersed within the fluid medium creating a homogeneous or at least a pseudohomogeneous mixture. The resulting mixture behaves as a single fluid phase eliminating or substantially reducing the need for complicated apparatus and mechanical mixing equipment generally required for handling heterogeneous reaction mixtures. In addition, the single homogeneous or pseudohomogeneous mixture reduces mass transfer resistances to levels substantially below those of heterogeneous reaction systems, thus facilitating rapid and uniform reactions and thereby eliminating or at least substantially reducing the need for oxidation catalysts. The single-phase system also allows for reduced residence times and/or reduced size for the reactor and associated equipment as compared with heterogeneous reaction systems. The high solvent power of the supercritical water also keeps organic intermediates well solvated and dispersed thereby eliminating char-forming reactions.

The process can be utilized for recycling pure or virgin rubber polymers such as to reduce waste and optimize product yield at rubber polymer manufacturing, compounding and production facilities, or to recycle rubber polymers containing normal amounts of conventional rubber compounding ingredients such as processing aids, vulcanizing agents, accelerators, antidegradants, fillers, softeners, etc.

To prevent undesirable reactions such as pyrolysis and charring, the reactants are preferably mixed so that the rubber polymer is rapidly brought to a sufficiently high temperature so that when the oxidant is brought into contact with the rubber polymer and water, the water is at supercritical conditions. That is to say, the temperature of the rubber polymer is preferably raised from near ambient conditions to the critical temperature of water as quickly as possible, and the amount of time wherein the oxygen is in contact with the rubber polymer at conditions below the critical temperature and pressure of water is preferably kept to a minimum. Preferably, the rubber polymer is rapidly brought to a temperature above the critical temperature of water (374° C.) by contacting the rubber polymer directly with supercritical water and thus raising the temperature of the mixture substantially instantaneously and minimizing or substantially eliminating char formation. The oxidant is preferably mixed with the rubber polymer-supercritical water mixture at or just before the inlet of the reaction vessel. Oxidation catalysts such as common metal oxides or supported metal catalysts which provide sufficient activity for oxidation can be used, but are generally unnecessary and not desired.

In the reaction vessel, the rubber polymers are broken down through chain scission (i.e., carbon-carbon bond scission), and devulcanization (i.e., sulfur-sulfur and carbon-sulfur bond scission) if a vulcanized rubber is used, into lower molecular weight organics and combustion products, with the product yield and distribution depending on the reaction parameters including temperature, pressure and reactant concentrations at the inlet, as well as the particular rubber polymer which is being reacted. Generally, for any particular rubber polymer suitably amenable to the process, the relative amounts of oxidant, water and rubber polymer, along with the inlet temperature and pressure, are optimized to promote carbon-carbon bond cleavage in the backbone of the rubber polymer and to promote sulfur-sulfur and carbon-sulfur bond cleavage if sulfur crosslinked rubbers are used, while minimizing other oxidation reactions such as complete oxidation to carbon dioxide and water. Accordingly, relatively small quantities of oxidant are used in the supercritical water reaction mixture in order to achieve partial, oxidative decoupling of the rubber polymer to maximize formation of lower molecular weight hydrocarbons and lower molecular weight oxygenated hydrocarbons.

While lower molecular weight product distributions predominantly containing hydrocarbons and oxygenated hydrocarbons containing 3–8 carbon atoms are generally preferred, for any particular rubber polymer the actual product distribution can be controlled by appropriate reactor design to vary the average residence time of the reactants and the residence time distribution, by appropriate selection of the oxidant to rubber polymer molar or weight ratio, by appropriate choice of operating temperatures, pressures and concentration, by selecting an appropriate oxidation catalyst in some cases, and by controlling various other parameters such as the reactant to solvent ratio.

The selective oxidative decoupling process in accordance with the invention generally occurs relatively rapidly, and relatively short residence times are required as compared to, for example, heterogeneous catalytic oxidation processes. The residence times, like the other process parameters, are dependent on the particular rubber polymer being reacted and are selected to maximize the desired product distribution or yield.

The process can be carried out in a batch, semi-batch, or continuous reaction system. Continuous stirred tank reactors, tubular flow reactors, and fluidized bed reactors, among others, can be utilized with the process. Primary reactor design considerations are the ability to rapidly contact the reactants and handle the temperatures, pressures, and corrosive effects of supercritical water solutions.

Because the reactions occur rapidly, heat losses are minimal and the products contain essentially all of the enthalpy of oxidation. Accordingly, in accordance with a preferred aspect of the invention, the enthalpy of oxidation can be recovered and used to preheat the reactants and to sustain the reactor temperature.

While the process can be used with virgin or pure rubber polymers, it is preferably used with waste rubber polymers which have been compounded with normal quantities of conventional compounding ingredients such as processing aids, vulcanizing agents, accelerators, anti-degradants, fillers, softeners, and the like. The process can be used for separating the conventional compounding ingredients from the rubber polymer and converting the rubber polymer to lower molecular weight compounds which can be used as a fuel or subsequently refined to obtain pure chemical feedstocks. Inorganic additives such as fillers, calcium carbonate and the like are generally insoluble in the supercritical water solution and can be recovered as a precipitated residue.

The invention thus provides a relatively simple process for recycling waste rubber material to recover useful low molecular weight components in a closed reaction system which is free of stack emissions to reduce landfill waste without generating air contaminants.

DETAILED DESCRIPTION OF THE INVENTION

The process of the invention generally comprises the steps of forming a homogeneous or pseudohomogeneous mixture of rubber, water and oxidant, and causing the mixture to undergo selective oxidation at supercritical conditions for water to break up (cause scission of carbon-carbon, carbon-sulfur, and sulfur-sulfur bonds) the rubber into lower molecular weight components with a relatively high product yield of lower molecular weight hydrocarbons and oxygenated hydrocarbons containing preferably from 3 to 8 carbon atoms. However, the process of the invention can also be performed in accordance with the general principles of the invention at subcritical conditions but require longer reaction times. The products generally include alkanes, alkenes, dienes, aromatics such as benzene, toluene and xylenes, and in generally progressively diminishing quantities oxygenated hydrocarbons such as alcohols, carboxylic acids, aldehydes and ketones, as well as small quantities of rubber fragments, carbon dioxide, water and other combustion products such as sulfur and nitrous oxides, and halide acids depending on the rubber which is reacted in the process.

Generally any natural or synthetic rubber, or synthetic elastomer can be processed in accordance with the invention to produce large yields of lower molecular weight hydrocarbons and oxygenated hydrocarbons preferably containing from about 3 to about 8 carbon atoms. The products of the process can be used as fuel such as a substitute for heating fuel, or can be subsequently refined or fractionated to produce a high-grade fuel substitute for gasoline, or to produce various commodity or specialty chemicals.

Rubber polymers which are suitable for processing in accordance with the invention include those made from one or more conjugated dienes having from 4 to about 10 carbon atoms, and one or more optional comonomers such as vinyl-substituted aromatics having from 8 to about 12 carbon atoms, acrylonitrile and derivatives thereof, as well as monoolefins having from 2 to about 6 carbon atoms, and the like; as well as halogenated derivatives of any of the above. Specific examples include natural rubber, polyisoprene or synthetic rubber, polybutadiene, poly(butadiene-co-styrene), poly(butadiene-co-acrylonitrile) poly(isobutylene-co-isoprene) or butyl rubber, EPDM rubber [poly(ethylene-co-propylene-co-diene )], neoprene or polychloroprene, silicon rubber (e.g., polydimethylsiloxane), polyalkylene sulfide (Thiokol®), polyester or polyether urethane rubbers, polyurethane thermoplastic elastomers, and the like, as well as various combinations thereof. Particularly preferred rubber materials for use with the process include styrene-butadiene, polybutadiene and neoprene rubbers. The rubber compositions suitable for processing with the invention can be either pure or virgin rubber polymers and, more typically, previously compounded rubber products, such as scrap tires, which are no longer useful for their intended purpose. The rubber compositions which can be subjected to the process of the invention include rubber compositions which have not been vulcanized and, more typically, vulcanized rubbers including rubber polymer compositions which have been vulcanized with elemental sulfur, thiuram disulfides or other sulfur-donating organic compounds, peroxides, dinitrosobenzene, or other known crosslinking or vulcanizing agents.

A wide range of rubber polymer compositions having diverse molecular weights can be processed in accordance with the invention, including low molecular weight materials at or near the oligomer range up to and including high molecular weight rubber polymers having some crystalline character. The rubber polymer materials which can be used include those containing various amounts of conventional compounding ingredients such as antimicrobials, antioxidants, antiozonants, color concentrates, colorants, pigments, fillers, softeners, ultraviolet stabilizers, flame retardants and the like.

The oxidant or oxidizing agent is preferably air, oxygen, or a mixture of oxygen and inert gases, but other oxidants such as peroxy compounds or oxygen generating species such as peroxides, e.g., hydrogen peroxide, benzoyl peroxide, dicumyl peroxide, etc.; perchlorates; permanganates, such as a potassium permanganate; ozone; and the like can be used including any compounds known to generate or release oxygen at reaction conditions. A conventional oxidation catalyst can also be used.

The relative amounts of water, rubber polymer material and oxidant are dependent upon the particular rubber polymer or polymers which are being reacted via the selective decoupling process of the invention and on the desired product distribution, e.g., molecular weight distribution of the products. Generally however, low amounts of oxidant combined with short residence time are utilized so as to promote or maximize carbon-carbon, carbon-sulfur and sulfur-sulfur bond breakage or cleavage and to inhibit or limit other undesirable reactions such as complete oxidation to carbon dioxide and water. In other words, the oxidant used is regulated such that the reaction is carried out to only a partial extent so as not to completely oxidize the end product. A suitable amount of oxidant are stoichiometric deficient amounts such as from about 5 or 10 percent to about 65 or 75 or 85 percent, desirably from about 15 to about 50 percent, and preferably from about 20 to about 40 percent of the total number of equivalents of the oxidant which are required to result in complete combustion of the rubber to water and carbon dioxide. Thus, a deficient equivalent amount of oxidant, which is nearly consumed or preferably completely consumed, is used to produce the above-noted product distribution, such as hydrocarbons or oxygenated hydrocarbons containing from about 2 or 3 to about 8 carbon atoms.

The exact amount of oxidant in the form of oxygen can vary over a wide range as from about 0.5 percent to about 95 percent by volume based upon the total volume of critical water and oxygen or oxidant, and the rubber polymer. Generally, low amounts of oxygen are preferred such as from about 0.5 to about 30 percent, and more desirably from about 5 to about 15 percent, by volume based upon the total volume of critical water, the oxidant, and rubber used.

The reaction is generally carried out at a temperature and at a pressure at, near to, or above the critical temperature (about 647° K.) and critical pressure (about 218 atmospheres) of water; however, conditions below the critical conditions are generally less effective.

The amount of rubber polymer material used relative to the amount of water in the reaction mixture can also vary depending on the particular rubber material being used and on the other operating parameters such as temperature, pressure, oxidant concentration, and chosen residence time. The amount of rubber used is further restricted by the energy balance. That is, the total amount of rubber used must be such that the temperature rise generated by the exothermic reaction is less than the maximum temperature needed to melt the oxidation vessel. This constraint depends on the rubber polymer weight, the heat of combustion associated with the particular rubber composition, the amount of oxidant used, the reactor pressure and the reaction starting temperature. However, the amount of rubber polymer material used in the reaction mixture is generally near the maximum amount which can be solubilized by or added to the supercritical water without losing the homogeneous single fluid phase character of the mixture. The maximum amount of rubber material which can be mixed into a given quantity of supercritical water can also be limited in some cases by the tendency of intermediate products of the selective oxidation process to react either with the rubber polymer, the oxidant and/or other intermediate products of the reaction to produce significant quantities of undesirable by-products. Typically, the amount of rubber polymer which can be added to the critical water to form the reaction mixture can range from about 0.1 or 1 percent to about 50 percent, and more preferably from 10 percent to 30 percent of the weight of the water and rubber polymer combined. This amount is generally from about 50 or 100 to about 1,200 or 2,000 parts by weight, desirably from about 150 to about 1,000 parts by weight, and preferably from about 200 to about 900 parts by weight per 100 parts by weight of rubber utilized.

The reaction time or residence time in the reactor depends upon various factors such as the amount of oxygen, the temperature and pressure of the reaction mixture, oxidant and rubber polymer concentration in the reaction mixture, and the like, and can generally range from about 3 seconds to about 1 hour. Most rubber materials can be processed within a residence time of 3 minutes. The residence time also depends upon the desired product distribution. Generally speaking, a long residence time tends to cause more $CO_2$ and $H_2O$ in the product, while a short residence time causes higher molecular weight product distribution. However, if it is too short, then high amounts of high molecular weight rubber fragments can be produced. The amount of carbon dioxide produced during the process is generally less than 20 percent, desirably less than 10 percent, and most preferably less than 5 percent by volume, i.e., at standard conditions (20° C. and one atmosphere).

Typical products from the process include alkanes, alkenes, dienes, aromatics, alcohols, carboxylic acids, aldehydes and ketones, all preferably having from about 3 to about 8 carbon atoms, as well as carbon dioxide, water and halide acids (when the rubber polymer includes halogens). Hydrocarbon and oxygenated hydrocarbon products containing from 3 to 8 carbon atoms generally comprise at least 30 percent by weight of the reaction product and more preferably comprise at least 50 or 70 percent by weight of the reaction product, and can, most preferably, comprise from up to about 80 or 90 percent of the reaction products. The term "reaction product" is limited to the products formed from breaking up the polymeric rubber in accordance with the method of the invention and specifically does not include the supercritical water or any metals, fibers, or other materials substantially inert to the reaction process. Trace amounts of methane, ethane, ethylene and higher hydrocarbons ($>C_8$) can also be obtained depending on the specific operating conditions.

Typical operating conditions are:

Temperature=374°–500° C., preferably 380° C. to 450° C.

Pressure=218–400 atm, preferably 220 to 270 atm

Mode: Continuous, batch, semi-batch

Feed: Premixed or in situ mixed

However, the process can also be operated under but near critical conditions, with or without a catalyst. The conditions are:

Temperature=200°–374° C., preferably 300°–374° C.

Pressure=70–218 atm, preferably 150–218 atm

Carrying out the process of the invention at subcritical conditions is generally not preferred, however, because larger residence times are required and/or lower product yields and lower product selectivity are achieved.

Figures 1, 2:
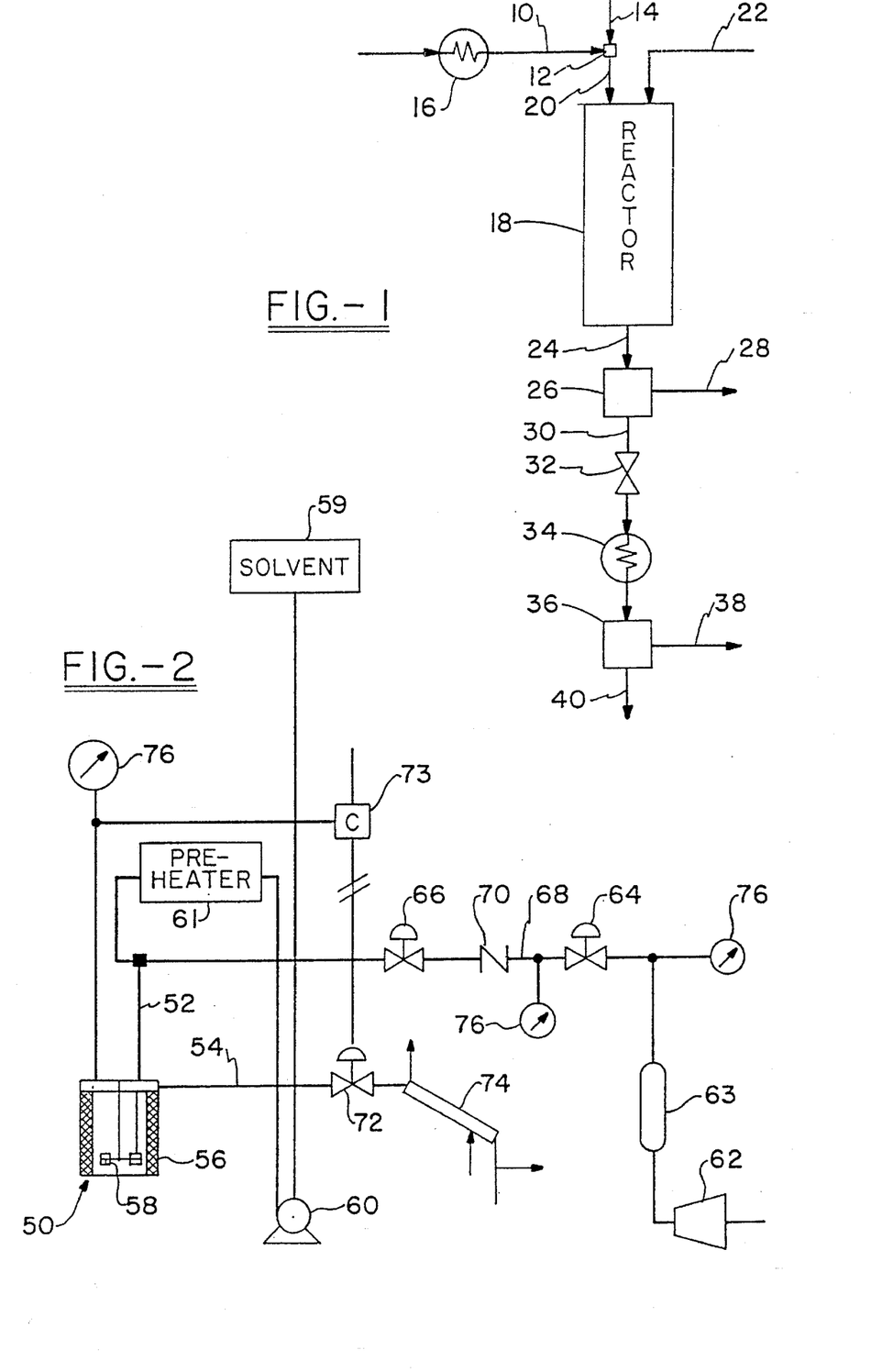
FIG. 1 is a schematic diagram of an apparatus for breaking down rubber polymers in accordance with the principles of the invention.
FIG. 2 is a schematic of a pilot scale apparatus for breaking down rubber polymers in accordance with the principles of the invention.

Shown in FIG. 1 is a simplified schematic representation of apparatus useful for practicing the invention in a continuous process mode. The rubber polymer or feed material containing rubber polymer along with additives and/or other impurities, including metals and fibers from, for example, scrap tires, is carried through conduit means 10 to mixing point 12 where it is preferably thoroughly mixed with water carried through conduit means 14. The rubber polymer is preferably comminuted, for example, to a particle size of less than about ½-inch, more desirably less than about ⅜-inch, and most desirably from about 300 microns to about ¹⁄₁₅-inch and is also preferably mixed with water to form a pumpable slurry. The rubber polymer can optionally be preheated at preheater 16 using thermal energy recovered downstream in the process. The water which is mixed with the rubber polymer is generally at a temperature and pressure near or above the critical temperature and pressure of water and preferably at a temperature and pressure sufficient to ensure that the reaction mixture is at least sufficiently near the critical conditions for water to ensure that critical conditions are reached in the reactor 18 upon the evolution of heat from the exothermic oxidation reactions. Most preferably, the temperature and pressure of the water carried in conduit means 14 are sufficiently high to ensure that the reaction mixture comprising the rubber polymer or feed material containing rubber polymer, along with additives and/or other impurities carried through conduit means 10 mixed with the water from conduit means 14 and entering reactor 18 through conduit means 20 are at or above the critical temperature and pressure of water. At or immediately prior to the inlet of the reactor an oxidant carried through conduit means 22 is mixed with the reaction mixture carried through conduit means 20. The reaction mixture and oxidant are preferably mixed with sufficient turbulence or mechanical agitation to ensure thorough macroscopic homogeneity of the rubber polymer, oxidant and solvent. The reactor 18 can, for example, be a plug flow reactor of sufficient length to provide for optimum conversion of the rubber polymer to useful lower molecular weight components.

Inorganic additives and/or impurities carried with or contained within the rubber polymer feed material generally become separated from the rubber polymer in the reactor. Because inorganic materials are not generally soluble in the supercritical fluid mixture, any inorganic materials entering the reactor with the rubber polymer are precipitated within the reactor and can be separated as a solid residue from the reactor outlet stream 24 at separator 26 and removed via conduit or conveyance means 28. Separator 26 can generally be any suitable conventional apparatus for separating solids from a fluid, such as filtering or centrifuge means.

Organic additives and/or impurities can also be handled by the apparatus of the invention. Generally, such organic additives or impurities will be oxidized and converted to lower molecular weight fragments and components which are carried along with the products and by-products in the fluid phase exiting from separator 26.

The reaction products in the fluid phase exit separator 26 via conduit means 30 and pass through pressure reducing means 32 which lowers the pressure of fluid to near ambient pressure. The fluid then flows into condenser 34 wherein the water is condensed to the liquid phase.

Separator 26 can be eliminated in the event that the rubber polymer feed material has relatively low amounts of inorganic precipitatable additives or impurities. Alternatively, solids and/or precipitated materials can be separated from the product stream downstream of the process.

In general, the liquid water and the organic products are generally immiscible and can be easily separated by conventional gas-liquid or liquid-liquid separating means 36 depending on the rubber polymer used and the resulting products. The product stream 38 can be subjected to various known unit operations, such as distillation, solvent extraction, chilling, etc. depending on the nature of the products, in order to achieve the desired degree of purity of the various components. The water stream can be suitably reheated and repressurized for reintroduction into the process via conduit means 14.

In accordance with a preferred aspect of the invention, heat removed from the process at condenser 34 can be recovered and used for preheating the rubber polymer feed material at preheater 16 and/or used for heating the water used as a solvent in the process.

The high temperatures, generally in excess of 374° C., and high pressures, generally in excess of 218 atmospheres, along with the corrosive nature of supercritical water, but more importantly subcritical water must be taken into consideration when designing the process apparatus for practicing the invention. In particular, Hastelloy C-276 has been found to be a suitable material for the construction of the reactor vessel and various other apparatus exposed to the supercritical water and/or reaction mixture and any wetted part which is exposed to subcritical water during start-up and shutdown.

The process can be used to recycle various rubber waste such as waste from molding operations, extrusion operations, and the like, instead of being disposed in accordance with stringent EPA requirements. The recovered products can then be separated, for example, with components thereof being returned to the rubber polymer manufacturing facilities to create virgin rubber polymers. By suitably adjusting parameters, the process can be utilized to achieve higher or lower molecular weight distributions of the product as desired to produce, for example, fuels or lubricants which can be used as a substitute for oil or gasoline.

FIG. 2 is a schematic representation of an apparatus used to study the selective oxidative decoupling of rubber in accordance with the invention. The system consists of three sections, an electrically heated oxidation vessel, a high-pressure solvent delivery system, and a water-cooled depressurization and collection chamber.

Bolt Closure Reactor

The vessel 50 depicted in FIG. 2 is a highpressure, 1000-cc Hastelloy C-276 steel bolt closure reactor manufactured by Autoclave Engineers Inc. The unit is fitted with ⅛" and ¼" Hastelloy C-276 feed delivery 52 and product outlet lines 54 respectively. The reactor is equipped with a thermowell (not shown), cooling coil (not shown), a top-mounted, air-driven agitator 58 (magne-drive), and a heating jacket 56 for start-up.

Solvent Delivery System

Water is delivered from a solvent reservoir 59 to the reactor via a high pressure micro-metering pump 60. This is capable of precisely delivering the solvent against a 5000 psi back pressure. A preheater 61 is provided to heat the water to a temperature sufficiently near the critical temperature to ensure that critical conditions are reached in the reactor. The flow capacity of this unit is 6000 cc (RTP)/hr at a motor speed of 85 RPM.

Oxygen is delivered to the reactor by a highpressure oxygen compressor 62 (Haskel AGT 30/75) via highpressure oxygen storage cylinder 63. This air-driven unit is capable of pressurizing pure oxygen to a maximum pressure of 5000 psi. The compressor is also equipped with a variable pressure safety relief valve and an automated air pilot switch. Both these safety features make it practically impossible to over-pressurize the oxygen storage cylinder 63, thereby decreasing the chances of failure due to spontaneous oxidation caused by over-pressurization of the components. A pressure regulator valve 64 and flow controller 66 are provided in the oxygen feed line 68. A check valve 70 is also provided in the oxygen feed line to prevent water from entering the oxygen storage cylinder 63 in the event of an unexpected loss of pressure. Gauges 76 are provided as appropriate to monitor pressure in the apparatus.

Product Depressurization

Depressurization of the oxidation unit is done with the use of a high-pressure control valve 72. A pneumatic controller 73 is used to operate in any one of the control actions; proportional, reset or derivative. Following the control valve, the hot products are directed to a water-cooled, high-pressure condenser 74. Here they are cooled to ambient conditions before being sent to a holding vessel for GC analysis.

The invention will be further illustrated but is in no way limited by the following examples and pilot plant apparatus used in association with the examples.

EXAMPLE 1

The selective oxidative decoupling process of the invention was performed using the apparatus shown in FIG. 2 and described hereinabove. A one-gram sample of a ground, scrap tire was charged to and oxidatively decoupled in the one-liter Hastelloy C-276 reactor. The sample was comprised of particles having a U.S. standard mesh size of from 14 to 35. After charging, the oxidation vessel was brought up to the desired extraction temperature and pressure by heating and by the constant addition of preheated, supercritical water. The process was operated at a temperature of 383° C. and 231 atmospheres (atm). The oxygen flow rate was maintained at 90 standard cubic centimeters (sccm) per minute and the reaction time was about one minute.

Figure 3:
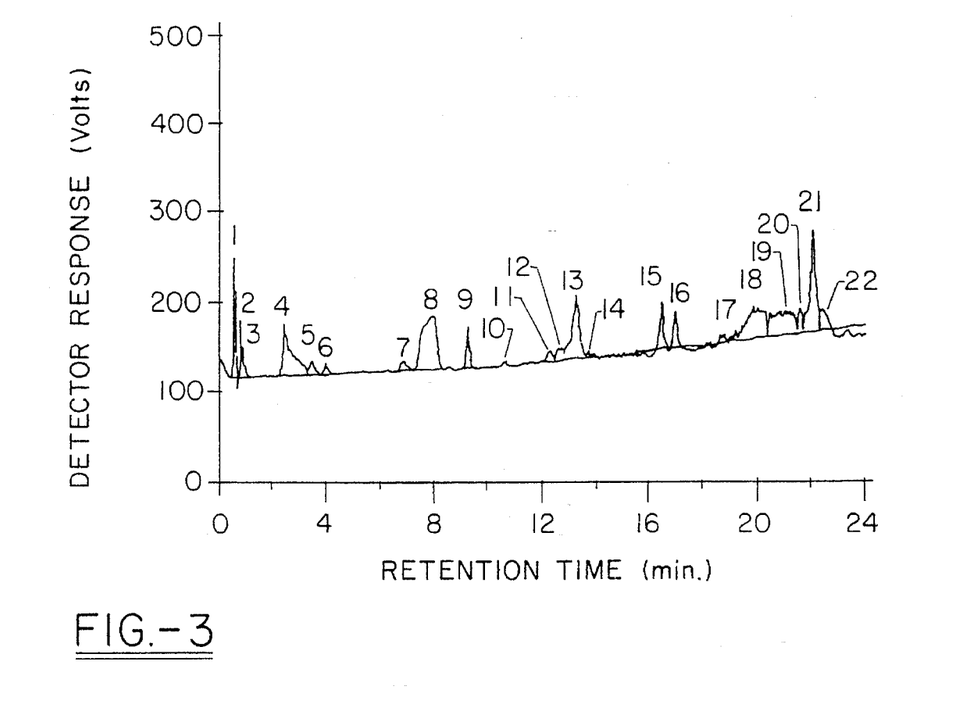
FIG. 3 is a gas chromatogram using a flame ionization detector, to identify the hydrocarbon and oxygenated hydrocarbon products of a one-gram tire sample oxidatively decoupled in accordance with the process of the invention using an oxygen flow rate of 90 sccm.
Figure 4:
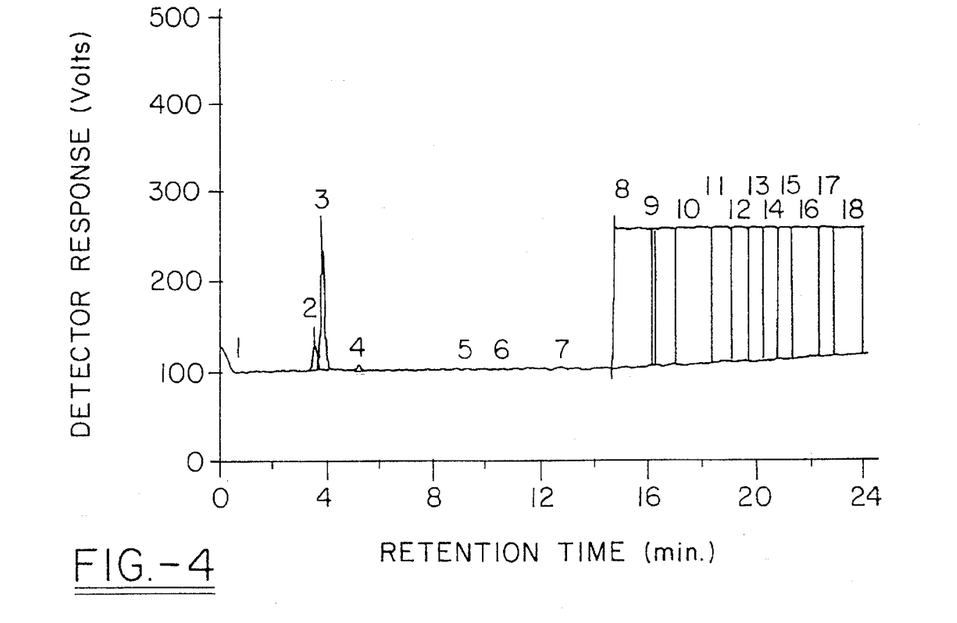
FIG. 4 is a gas chromatogram using a thermal conductivity detector to identify nitrogen, carbon monoxide, and carbon dioxide in the reaction products of a onegram tire sample oxidatively decoupled in accordance with the process of the invention using an oxygen flow rate of 90 sccm.

The products were analyzed using a gas chromatograph and the resulting chromatograms are shown in FIGS. 3 and 4. A flame ionization detector was used for identifying the hydrocarbon and oxygenated hydrocarbon products of the reaction. Nitrogen, carbon monoxide, and carbon dioxide products were identified using a thermoconductivity detector. The peak identifications and area counts are given in Tables I-A and I-B.

A gravimetric determination of the reaction products indicate that 82 percent, based on the original mass of the polymeric rubber material fed to the reactor, by weight of the reaction products were hydrocarbons and oxygenated hydrocarbons having from 1 to 7 carbon atoms. Carbon dioxide and water formation represented less than 5 percent of the mass of the product. The pH of the water recovered from the process was 4.3 indicating that small amounts of inorganic acids such as hydrochloric acid or sulfuric acid were probably formed during the process.

EXAMPLE 2

Figure 5:
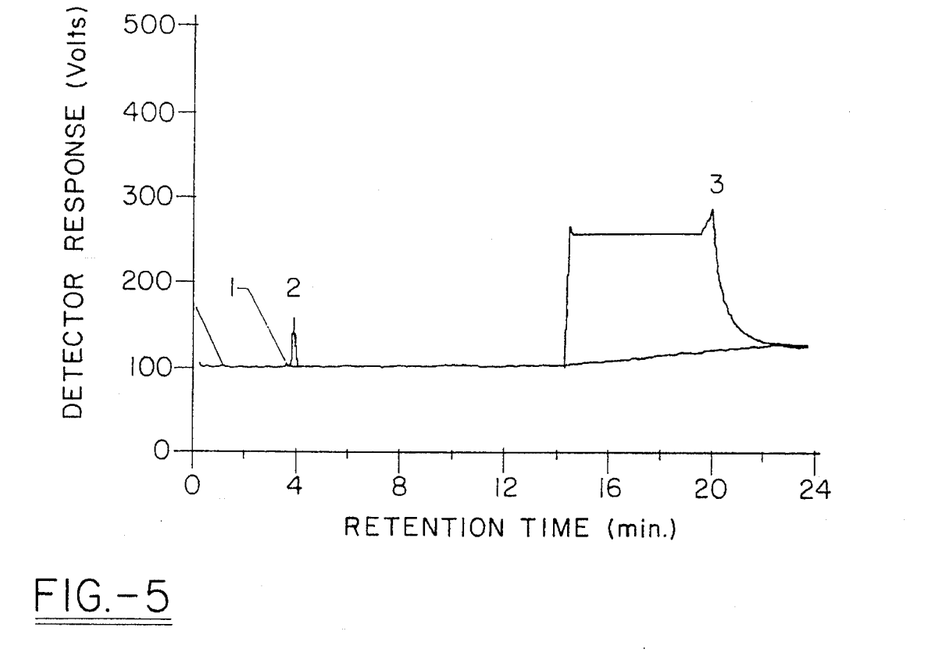
FIG. 5 is a gas chromatogram using a flame ionization detector, to identify the hydrocarbon and oxygenated hydrocarbon products of a one-gram tire sample oxidatively decoupled in accordance with the process of the invention using an oxygen flow rate of 180 sccm.
Figure 6:
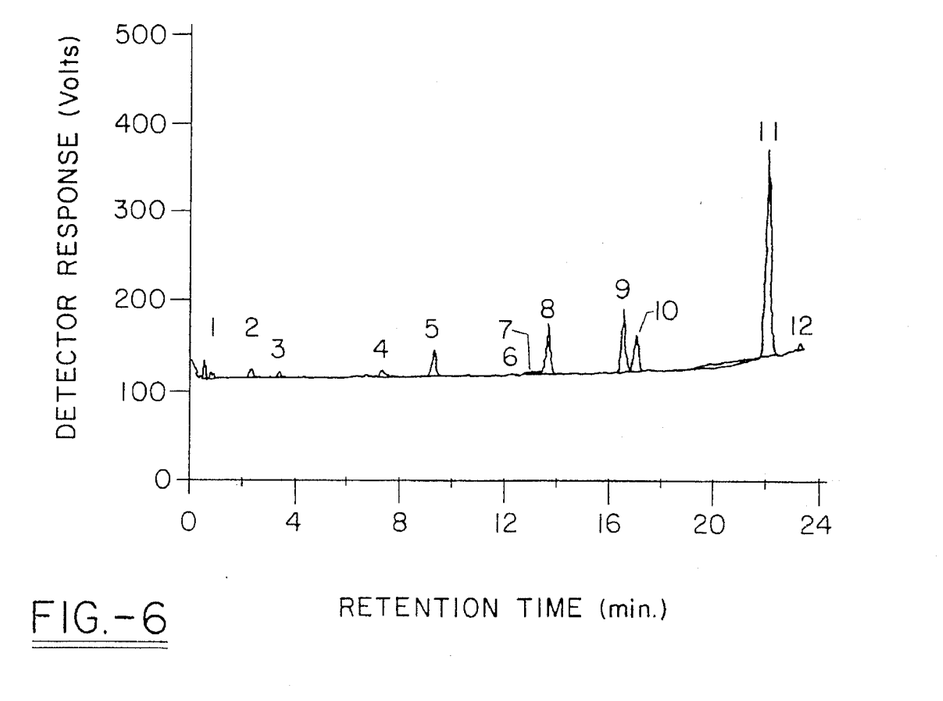
FIG. 6 is a gas chromatogram using a thermal conductivity detector to identify nitrogen, carbon monoxide, and carbon dioxide in the reaction products of a one-gram tire sample oxidatively decoupled in accordance with the process of the invention using an oxygen flow rate of 180 sccm.

A one-gram sample of a spent tire was ground to a U.S. standard mesh size of between 14 and 35 and charged to the one-liter Hastelloy C-276 reactor. Supercritical water was introduced to the reactor and the process was run at a temperature of 383° C. and a pressure of 231 atm. The oxygen flow rate was maintained at 180 sccm per minute and the retention time was 15 seconds. The products were analyzed utilizing gas chromatography with the resultant chromatograms shown in FIGS. 5 and 6. Peak identification and the associated area counts are shown in Tables 2-A and 2-B.

A gravimetric determination of the reaction products indicate that 76 percent, based on the original mass of the polymeric rubber material fed to the reactor, by weight of the reaction products were hydrocarbons and oxygenated hydrocarbons having from 1 to 7 carbon atoms. Carbon dioxide and water formation represented less than 3 percent of the mass of the product. The pH of the water recovered from the process was 4.6 indicating that small amounts of inorganic acids such as hydrochloric acid or sulfuric acid were probably formed during the process.

TABLE I-A

| Peak # | Species | Area Count |
|---|---|---|
| 1 | Methane | 1230.961 |
| 2 |  | 45.997 |
| 3 | Ethylene | 37.603 |
| 4 | Ethane | 1492.628 |
| 5 | Propylene | 263.323 |
| 6 | Propane | 144.676 |
| 7 | Iso-butane | 196.786 |
| 8 | Butadiene | 2258.61 |
| 9 | Isopentane | 419.043 |
| 10 |  | 68.129 |
| 11 | Pentene | 40.777 |
| 12 | Pentane | 197.013 |
| 13 | Pentadiene] | 1619.436 |
| 14 |  | 641.621 |
| 15 | Iso-hexane | 400.691 |
| 16 | Hexene | 282.974 |
| 17 | Hexane | 140.516 |
| 18 | Benzene | 1585.636 |
| 19 | Cyclohexane | 1529.132 |
| 20 |  | 337.913 |
| 21 | Iso-heptane | 1966.692 |
| 22 | Heptane | 344.583 |
| 23 | Toluene | 1512.424 |

TABLE I-B

| Peak # | Species | Area Count |
|---|---|---|
| 2 | Nitrogen | 382.602 |
| 3 | Carbon Monoxide | 1681.463 |
| 8–19 | Carbon Dioxide | 87940.466 |

TABLE II-A

| Peak # | Species | Area Count |
|---|---|---|
| 1 | Ethane | 307.153 |
| 2 | Propylene | 39.394 |
| 3 | Propane | 23.339 |
| 4 | Iso-butane | 60.8 |
| 5 | Butadiene | 829.868 |
| 6 |  | 35.761 |
| 7 | Iso-pentane | 299.592 |
| 8 | Pentene | 73.851 |
| 9 |  | 68.076 |
| 10 | Pentane | 296.033 |
| 11 |  | 308.173 |
| 12 |  | 407.308 |
| 13 | Pentadiene | 1206.569 |
| 14 |  | 216.633 |
| 15 | Iso- (or tertiary) -hexane | 527.455 |
| 16 | Hexene | 986.523 |
| 17 | Hexane | 622.909 |
| 18 | Benzene | 47.936 |
| 19 | Iso-heptane | 2369.83 |
| 20 | Heptane | 137.9 |

TABLE II-A-continued

| Peak # | Species | Area Count |
|---|---|---|
| 21 | Toluene | 1416.082 |

TABLE II-B

| Peak # | Species | Area Count |
|---|---|---|
| 1 | Nitrogen | 52.082 |
| 2 | Carbon Monoxide | 443.775 |
| 3 | Carbon Dioxide | 26.68 |

While in accordance with the Patent Statutes, a preferred embodiment and best mode has been presented, the scope of the invention is not limited thereto, but rather is measured by the scope of the attached claims.

What is claimed is:

1. A process for reacting rubber polymers to obtain high product yields of hydrocarbon and oxygenated hydrocarbons containing from 3 to 8 carbon atoms, the process comprising the steps of:

forming a reaction mixture of a vulcanized rubber polymer, water at or near supercritical conditions, and an amount of an oxidant which is sufficiently low to inhibit complete oxidation of the vulcanized rubber polymer, reacting said vulcanized rubber polymer with said oxidant in the presence of said water at a temperature of from about 200° C. to about 500° C., and at a pressure of from about 70 atmospheres to about 400 atmospheres, decoupling at least carbon to sulfur bonds of said vulcanized rubber polymer, producing at least 30 percent by weight of $C_3$–$C_8$ hydrocarbon compounds and $C_3$–$C_8$ oxygenated hydrocarbon compounds producing less than 20 percent by volume of carbon dioxide based upon the total volume of said reaction products; and recovering said hydrocarbon and oxygenated hydrocarbon ($C_3$–$C_8$) compounds.

2. A process according to claim 1, wherein the rubber polymer comprises a homopolymer or copolymer of one or more halogenated or non-halogenated conjugated dienes having from 4 to about 10 carbon atoms and optionally including one or more comonomers, or a silicon rubber.

3. A process according to claim 2, wherein said temperature is from about 374° C. to about 500° C., wherein said pressure is from about 218 atmospheres to about 400 atmospheres, and wherein said oxidant comprises air, oxygen, a mixture of oxygen and inert gases, peroxides, perchlorates, permanganates, ozone, or combinations thereof.

4. A process according to claim 3, wherein the amount of said carbon dioxide in said reaction products is less than 10 percent by volume, and wherein the weight of said $C_3$ to $C_8$ reaction products is at least 50 percent.

5. A process according to claim 4, wherein said oxidant is air, or oxygen, and wherein said rubber polymer is styrene-butadiene rubber, butadiene rubber, neoprene rubber, natural rubber, polyisoprene rubber, or combinations thereof.

6. A process for reacting rubber polymers to obtain product yields of hydrocarbons and oxygenated hydrocarbons, comprising the steps of:

forming a reaction mixture of a vulcanized rubber polymer, water at or near supercritical conditions, and from about 5 percent to about 85 percent of an oxidant based on the total equivalent amount of said oxidant which would result in complete combustion of said vulcanized rubber polymer to water and carbon dioxide;

reacting said vulcanized rubber polymer with said deficient amount of said oxidant in the presence of said water at a temperature of from about 200° C. to about 450° C. at a pressure of from 70 atmospheres to about 400 atmospheres, decoupling at least carbon to sulfur bonds of said vulcanized rubber polymer;

producing at least 50 percent by weight of $C_3$ to $C_8$ hydrocarbon compounds and $C_3$ to $C_8$ oxygenated hydrocarbon compounds;

producing less than 20 percent by volume of carbon dioxide in the reaction products based upon the total volume; and recovering said $C_3$ to $C_8$ hydrocarbon and oxygenated hydrocarbon compounds.

7. A process according to claim 6, wherein said deficient oxidant equivalent amount is from about 10 percent to about 65 percent.

8. A process according to claim 7, wherein said temperature is from about 374° C. to about 450° C., wherein said pressure is from about 218 atmospheres to about 400 atmospheres.

9. A process according to claim 8, wherein said deficient oxidant equivalent amount is from about 15 percent to about 50 percent, and wherein the amount of carbon dioxide is 10 percent or less by volume.

10. A process according to claim 9, wherein said deficient oxidant equivalent amount is from about 20 percent to about 40 percent, and wherein said oxidant is air or oxygen.

11. A process according to claim 6, further comprising the step of comminuting the rubber polymer material and mixing it with a fluid to form a pumpable composition, before forming the reaction mixture.

12. A process according to claim 10, wherein the rubber polymer material contains inorganic additives, and further comprising the steps of precipitating the inorganic materials from the reaction mixture and separating the precipitated materials from the reaction products.

13. The reaction product of at least one rubber in the presence of water and from about 5 percent to about 70 percent of an amount of at least one oxidant based on an amount of said oxidant resulting in complete combustion of said rubber to water and carbon dioxide, and wherein said reaction is carried out at a temperature of from about 200° C. to about 450° C. at a pressure of from about 70 atmospheres to about 400 atmospheres, said reaction product containing at least 30 percent by weight of decoupled rubber polymers in the form of $C_3$ to $C_8$ hydrocarbon compounds and oxygenated hydrocarbon compounds, and said reaction product containing 20 percent or less by volume of carbon dioxide.

14. The reaction product of claim 13, wherein the amount of said oxidant is from about 15 to about 50 percent, wherein said oxidant is air or oxygen, wherein said temperature is from about 374° C. to about 450° C., wherein said pressure is from about 218 atmospheres to about 400 atmospheres, wherein said rubber is styrene-butadiene rubber, butadiene rubber, neoprene rubber, natural rubber, polyisoprene rubber, or combinations thereof, wherein the amount of said $C_3$ to $C_8$ hydrocarbon compounds and oxygenated hydrocarbon compounds is at least 50 percent by weight, and wherein the amount of carbon dioxide is 10 percent or less by volume.

* * * * *